United States Patent [19]

Kikyotani et al.

[11] Patent Number: 5,208,160

[45] Date of Patent: May 4, 1993

[54] METHODS AND APPARATUS FOR THE CONTINUOUS TREATMENT OF BIOLOGICAL SAMPLES

[75] Inventors: Sho Kikyotani; Tatsuo Yamamoto, both of Osaka, Japan

[73] Assignee: Sekisui Kagaku Kogyo Kabushiki Kaisha, Osaka, Japan

[21] Appl. No.: 184,835

[22] Filed: Apr. 22, 1988

[30] Foreign Application Priority Data

Apr. 22, 1987 [JP] Japan ................................. 62-99446
May 13, 1987 [JP] Japan ................................ 62-116417
May 13, 1987 [JP] Japan ................................ 62-116418

[51] Int. Cl.$^5$ ................................................ C12N 1/08
[52] U.S. Cl. .................................... 435/270; 435/259;
435/262; 530/412; 530/413; 530/415; 210/638;
210/656; 210/660; 210/669
[58] Field of Search ........................ 435/259, 262, 270;
530/412, 413, 415; 210/638, 656, 660, 669;
536/27

[56] References Cited

U.S. PATENT DOCUMENTS

| 4,341,635 | 7/1982 | Golias ........................ 210/656 |
| 4,591,442 | 5/1986 | Andrews ...................... 210/656 |
| 4,900,435 | 2/1990 | Anderson ................. 436/161 X |
| 4,900,446 | 2/1990 | Anderson ................. 436/161 X |

FOREIGN PATENT DOCUMENTS

| 7006281 | 5/1981 | Australia . |
| 3096684 | 7/1984 | Australia . |
| 3096684 | 3/1987 | Australia . |
| 0268946 | 6/1988 | European Pat. Off. . |
| WO83/00023 | 1/1983 | PCT Int'l Appl. . |

OTHER PUBLICATIONS

Pharmacia, Affinity Chromatography, principles & methods p. 85, 1986.
Cowling, Nucleic Acids, Chap. 18, p. B345-B372, 1983 Journal of Chromatography, vol. 22 B, edited by E. Heffmann, Elsevier Sci. Publ.
Analabs Chromatography, Chemicals and Accessories Catalog (1987) p. 248.
Jones et al., "Automating the Purification . . . of Synthetic DNA", *Biol. Technology*, vol. 5 (1987) pp. 67–70.
Tekkanat et al., "Isocratic Separation . . . by Automated Liquid Chromatography", *Clinical Chemistry*, vol. 34 (1988) pp. 925–932.
Ullman et al., "High Performance Liquid Chromatography" in Textbook of Clinical Chemistry (W. B. Saunders 1986) pp. 159–172.
Robert K. Scopes, *Protein Purification*, Principles and Practice, p. 13.
Journal of Chromatography, vol 174, No. 1, 1979 pp. 177–186, Elsevier Scientific Publishing Co., Amsterdam, NL; F. A. Beland et al: "Rapid Isolation of Carcinogen-bound DNA and RNA by Hydroxypatite Chromatography".
Cancer Letters, vol. 26, No. 3, 1985, pp. 335–341, Elsevier Scientific Publishers Ireland Ltd., IL; A. A. Potter et al: "A Rapid Method for the Extraction and Purification of DNA from Human Leukocytes".

*Primary Examiner*—Esther L. Kepplinger
*Assistant Examiner*—Carol A. Spiegel
*Attorney, Agent, or Firm*—Morrison & Foerster

[57] ABSTRACT

An apparatus for the treatment of biological samples comprises: at least one column having an adsorbent layer made of adsorbent that fills a part of said column, and a reservoir forming the other part of said column; at least one vessel connected to said reservoir, said vessel being disposed so as to contain said samples to be supplied to said reservoir and/or media for treating said samples; a means for supplying said samples and/or media for treating said samples from said vessel to said reservoir; and a means for controlling said supply means. A method for the treatment of biological samples involves the use of the above-mentioned apparatus. With the use of the apparatus, the analysis of samples and also the isolation of desired substances from samples could be done automatically with accuracy in a simple procedure.

8 Claims, 7 Drawing Sheets

METHODS AND APPARATUS FOR THE CONTINUOUS TREATMENT OF BIOLOGICAL SAMPLES

BACKGROUND OF THE INVENTION

1. Field of the Invention

This invention relates to an apparatus for the treatment of biological samples, and in particular, to an automated apparatus for the treatment of samples, with a number of samples being treated at the same time, and with treatment being continuous; and to treatment methods using the same, and in particular, methods for the analysis and purification of samples from living organisms with the use of such an apparatus.

2. Description of the Prior Art

Among chromatography methods for separating or analyzing a desired substance in a sample a method using high-pressure liquid chromatography (HPLE) by which there can be a sending-liquid operation, an elution operation, and an eluate analysis operation, gives high performance, and its reproducibility is superior, so the method is widely used. However, before samples are supplied to the HPLC apparatus, in order to prevent damage to the separation column by the large amount of impurities contained in the samples, the samples must be treated. Also, the treatment of the column before its reuse is complicated.

In recent years, with the development in purification and separation techniques, there have been methods developed in which small columns are used, rather than expensive equipment such as HPLC, and with simple column operations, analysis can be done with relative accuracy. Small columns are small plastic open columns filled with packing material, and are now commercially available as disposable columns. However, analysis by small columns is always done by batchwise operations. Therefore, when a number of samples are to be analyzed, each sample, the washing liquid, the eluent, etc., must be at constant volumes, and supplied to the column in the proper order, which causes difficulties. Also, by this method, because it is difficult to carry out the treatment under uniform conditions, analytical accuracy is poor, and reproducibility is inferior. Thus, automatic analytical methods using small columns are needed, but the methods have not yet been realized.

SUMMARY OF THE INVENTION

The apparatus of this invention, which overcomes the above-discussed and other numerous disadvantages and deficiencies of the prior art, which comprises: at least one column with an adsorbent layer made of adsorbent that fills a part of the column, and a reservoir forming the other part of the column; at least one vessel connected to the reservoir, the said vessel being disposed so as to contain the samples and/or reagents for treating the samples to be supplied to said reservoir; a means for supplying the samples and/or reagents for treating the samples from said vessel to the reservoir; and a means for controlling the supply means.

In a preferred embodiment, the column is held in a column holder that is connected with an agitator.

The method for the treatment of biological samples of this invention by the use of the above-mentioned apparatus comprises the steps of: supplying the samples from the vessel to the reservoir via the supply means or supplying the samples directly to the reservoir; allowing the samples to permeate the adsorbent layer of the column, which causes the adsorbent to adsorb components of the samples; and eluting the components from the adsorbent layer by supplying the reagents for treating the samples from the vessel to the adsorbent layer via the supply means, the said supply of the samples and the media by the use of the supply means being controlled by the controlling means.

The method for the treatment of biological samples of this invention by the use of the above-mentioned apparatus comprises the steps of: supplying the samples from the vessel to the reservoir via the supply means or supplying the samples directly to the reservoir; allowing the samples to permeate the adsorbent layer of the column, which causes the adsorbent to adsorb components of the samples; supplying reagents for washing from the vessel to the adsorbent layer of the column via the supply means, so that the adsorbent layer is washed with the reagents for washing; and eluting the components from the adsorbent layer by supplying the reagents for treating the samples from the vessel to the adsorbent layer via the supply means, the said supply of the samples and the reagents by the use of the supply means being controlled by the controlling means.

In a preferred embodiment, the samples supplied to the reservoir of the column are pretreated in said reservoir with the use of reagents for pretreating said samples, and the reagents are supplied from the vessel to the reservoir via the supply means or supplied directly to the reservoir.

In a preferred embodiment, samples contain cells, and said cells are lysed when pretreated in the reservoir, by the use of reagents for pretreating said samples.

In a preferred embodiment, the samples contain DNA, and the DNA is purified.

In a preferred embodiment, the adsorbent is hydroxyapatite, and reagents for treating the samples are salt solutions that strongly interact with said adsorbent.

In a preferred embodiment, the cation component of the salt is ammonium or an amine, and the anion component of the salt is a volatile acid.

Thus, the invention described herein makes possible the objectives of: 1) providing an automated apparatus for the treatment of biological samples that can treat a number of samples at the same time, continuously, 2) providing an apparatus for treatment of samples and methods for such treatment in which, for the separation of desired substances from biological samples or the analysis of said samples, a pretreatment step, and analysis or separation steps are carried out continuously and automatically, so that analysis or separation can be carried out in a short period of time; and 3) providing an apparatus and methods for the separation of DNA from samples derived from living organisms in a short period of time, with high purity and a simple procedure.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

This invention was completed based on the inventors' knowledge that, for example, vessels that contain reagents for treating samples can be connected via a reagent-supply means to a single small column or a number of small columns filled with packing material (e.g., an adsorbent), and when the reagent supply means is controlled by a control means, it is possible to conduct an automated analysis of biological samples or an automated separation of specific substances from the said samples. Moreover, this invention was completed based on the knowledge that if it is possible to pretreat the samples in an empty space (i.e., reservoir) of the small column(s) mentioned above that is not filled with adsorbent, it will be possible to simplify the treatment of samples.

Figure 1:
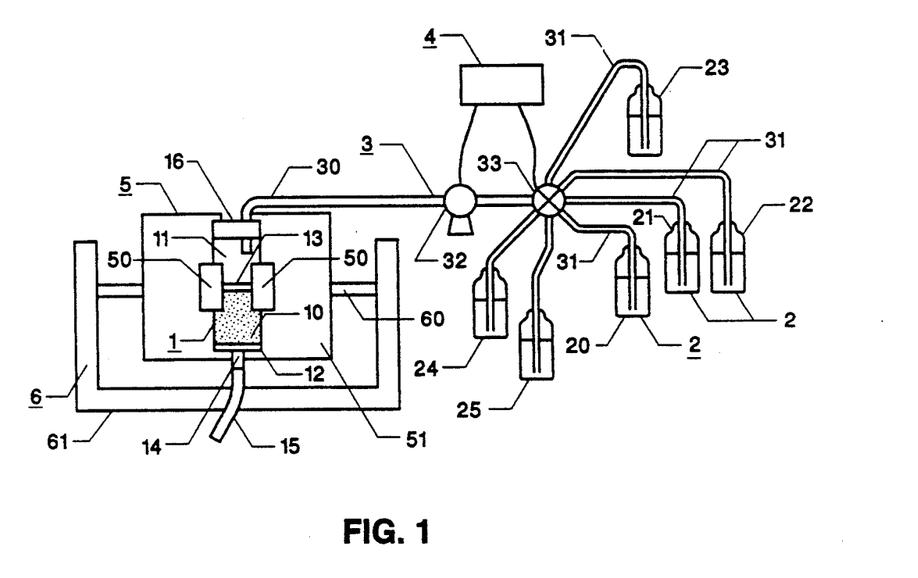
FIG. 1 shows a schematic diagram of an example of the apparatus for the treatment of biological samples of this invention.

FIG. 1 shows an apparatus of this invention for the treatment of biological samples that has, for example, a column 1 that has an adsorbent layer 10 and a reservoir 11, a number of vessels 2 that contain reagents for the treatment of samples or samples to be supplied to the column 1, a supply means 3 that supplies the reagents for the treatment of samples from the vessels 2 to the column 1, and a control means 4 that controls the supply means 3, etc..

Figure 2A:
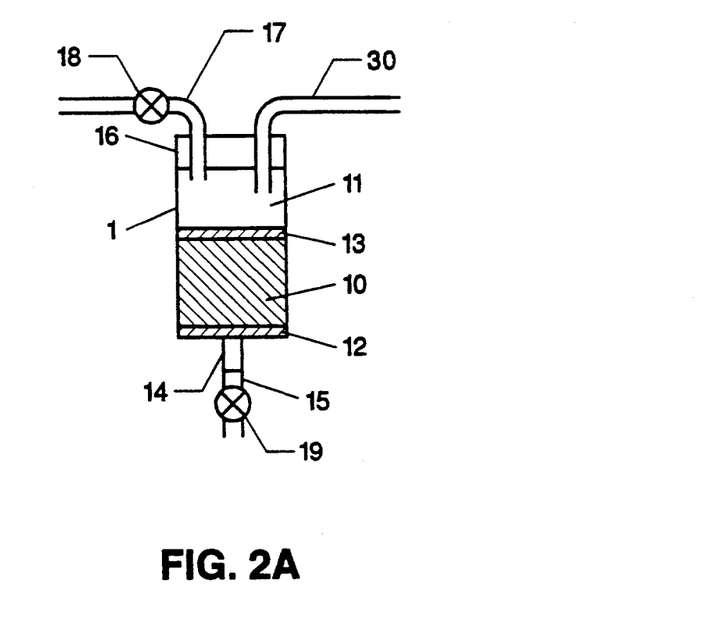
FIGS. 2A, 2B and 2C show examples, in cross-section, of the column used in the apparatus of this invention.

As shown in FIG. 2A, for example, the column 1 has an adsorbent layer 10 made of an adsorbent that fills a part of the column, and also a reservoir 11 that forms the other part of the said column. The samples can be pretreated in the reservoir 11. Components to be separated from the samples are adsorbed on the adsorbent layer 10. Filters 13 and 12 are disposed in the space between the adsorbent layer 10 and the reservoir 11 and in the space between the adsorbent layer 10 and the end of the column, respectively. At the bottom of column 1 (that is, at the end of the column toward the adsorbent layer 10), there is an outlet 14 for the outflow of eluate. There is a collection tube 15, with a valve 19 that is connected to the outlet 14. At the upper end of column 1, there is a stopper 16 by which the inside of column 1 can be made air-tight, and there is also a system made up of tube 17 and valve 18 for the purpose of opening column 1 to atmospheric pressure. The column 1 is connected to a tube 30, which supplies reagents (pretreatment liquid, washing liquid, eluent, liquid for the regeneration of the column, etc.) for the treatment of samples.

Figure 2B:
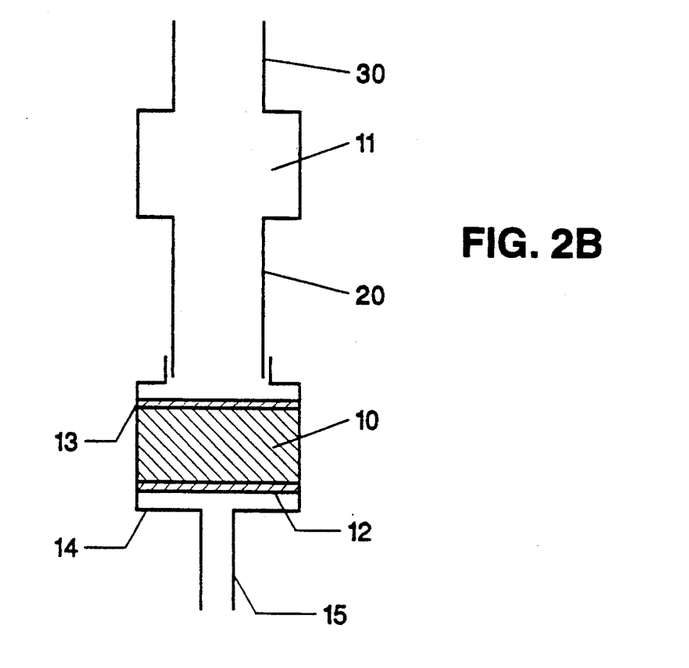
Figure 2C:
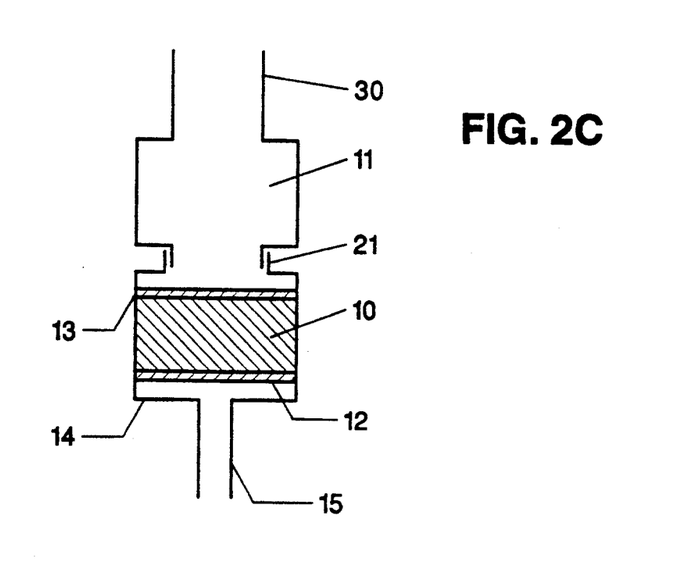

This column 1 has, for example, as shown in FIG. 2B, the adsorbent layer 10 and the reservoir 11 in separate parts, which can be connected by a tube 20 of appropriate length. Moreover, for example, it is acceptable if the adsorbent layer 10 and the reservoir 11 are separate but connected by connecting section 21 to be almost one part, as shown in FIG. 2C.

The plural vessels 2 mentioned above are all connected to the reservoir 11 of the column 1 via tubes 31 which are included in the supply means 3. These vessels can, for example, be vessels 20, 21, 22, 23, 24 and 25, which contain washing liquid, eluent, liquid for the regeneration of the column, or the like. These various solutions are reagents for the treatment of samples. When there is a large volume of sample, a vessel or vessels to contain the said sample are added to this system. If the vessels are supplied with sample, the sample supply can also be automated. When reagents for sample treatment other than the above are used, these reagents for sample treatment are put in separate vessels connected to the same tube 31.

The supply means 3 is provided to supply sample and the reagents for sample treatment in the vessels 2 to the column 1. This supply means 3 is composed of, for example, tubes 30 and 31, pump 32, and valve 33. One end of the tube 30 is connected to the reservoir 11 by being passed through the column stopper 16 of the column 1. The other end is connected to the tube 31 via valve 33. The tube 31 is connected to the vessels 20, 21, 22, 23, 24 and 25. The pump 32 can be disposed on a given portion of the tube 30. The reagents for sample treatment or the samples in the vessels are supplied from the vessels 2 by the power of the pump mentioned above through the tubes 31 and 30 to the column 1. The valve 33 is a switching valve that can be switched so that a particular vessel among the plural vessels 2 can be connected with column 1. The pump 32 need not be a high-grade pump such as one for use in HPLC; the pump can be an ordinary one that can be connected to a number of tubes. By operation of the valve 33, any of the plural vessels 2 can be selectively connected to the column 1 via the tubes 31 and 30, depending on need. As this valve, ordinarily, a switchable valve can be used.

Control means 4 can, for example, be a computer, and is connected to pump 32, valve 33, and the column agitator 6 and fraction collector 7 that will be described below. This control means 4 is provided to control the flow rates maintained by the pump, the switching of the valves, the movements of the fraction collector, and the like. This control means 4 makes possible the automation of the amount of sample or reagents for the treatment of sample by the pump and the selective connection of the vessels and the column; for example, a control means that is a computer selects a certain vessel among the plural vessels 2, based on information that was previously input thereinto, and supplies a fixed amount of the reagents for sample treatment or of the sample in the vessel to column 1. Also, when a number of samples are being analyzed by the use of a number of columns and a fraction collector, the control means 4 can select the desired collection vessel 70.

Figure 3:
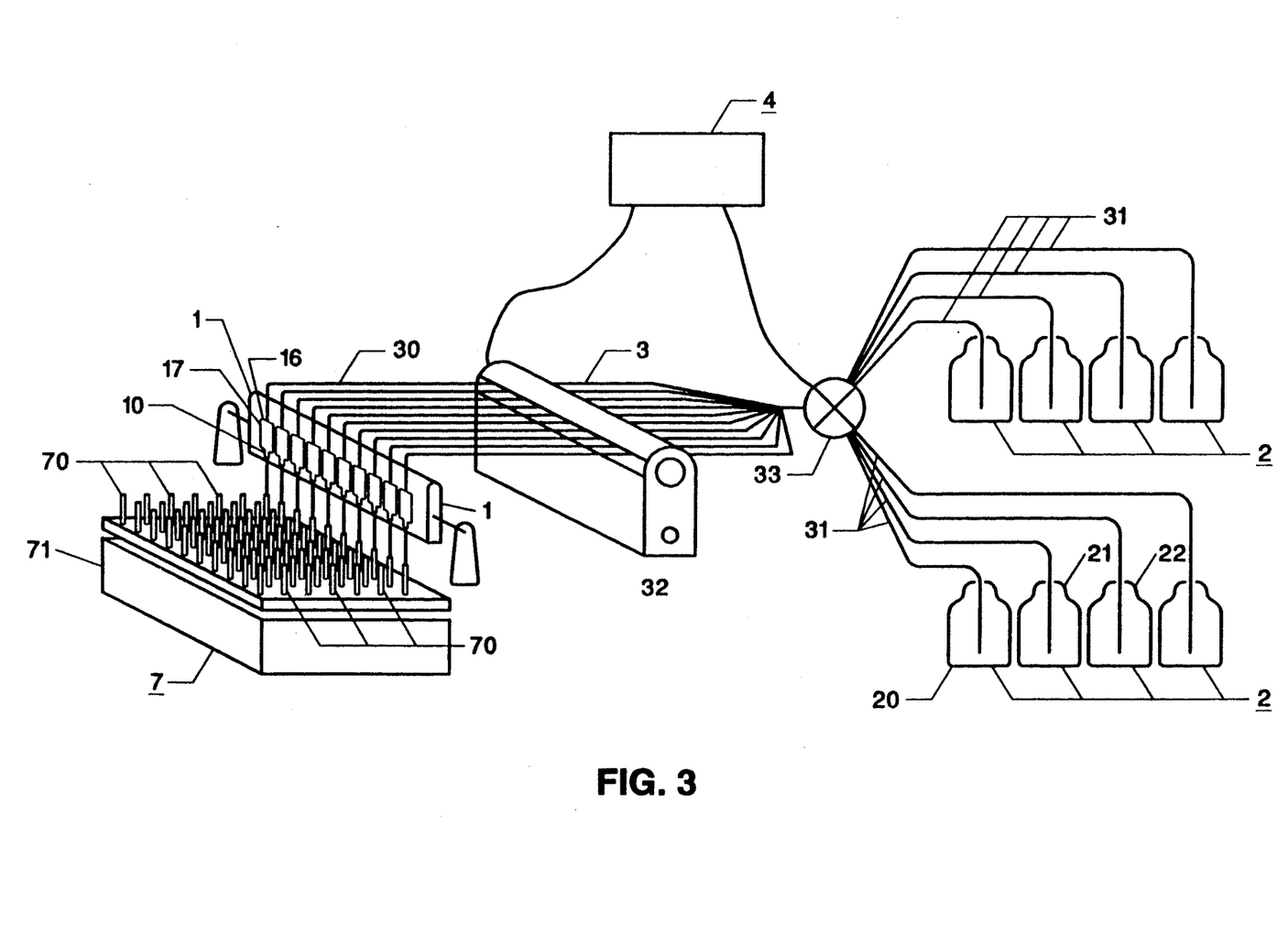
FIG. 3 shows a schematic diagram of another example of the apparatus of this invention.

Column 1 is usually supported by a column holder 5, which has a pair of holders 50 so that column 1 can be held vertically, and a fixed plate 51 at one side of which each holder 50 is fixed. This column holder 5 can also be connected to agitator 6. The agitator 6 effectively agitates and mixes the sample charged in the reservoir 11 of the column. Therefore, pretreatment (which will be described below) of the sample is carried out effectively. Furthermore, the adsorption of certain components in the sample can be accelerated, and the washing of the adsorbent by the reagents for sample treatment can also be accelerated. This agitator 6 is connected with the column holder 5. The agitator 6 has a revolving shaft 60 that is provided in the center portion of the fixed plate 51 of the column holder 5, and a supporter 61 that rotatably supports shaft 60 at both of its ends. For this column holder 5 and agitator 6, the holders 50 are supported so that they can rotate around the supporters 61 via the fixed plate 51 and the revolving shaft 60. Accordingly, this agitator 6 can agitate column 1 by the rotation of the revolving shaft 60. As column 1, a number of columns can be used, and in that case, so that the collection of eluate from the column proceeds readily and efficiently, a fraction collector can be provided. An example of the apparatus of this invention that has such a fraction collector is shown in FIG. 3, wherein a number of tubes 30 are connected to a number of columns and the valve 33 via pump 32. The fraction collector 7 that is provided at the outflow end of the plural columns 1 is placed in such a way that the plural columns 1 correspond to fraction tubes of the fraction collector 7.

The apparatus and the methods of this invention can be used for the analysis of samples of various biological origins and also for the separation of desired substances from said samples. With this invention, because the treatment apparatus has a column with a reservoir, it is possible to carry out the pretreatment of samples before the treatment of the samples in this reservoir. The pretreatment of the samples can involve, for example, the lysis of cells of, for example, microorganisms, etc., the denaturation of protein, an extraction step, and the like. The apparatus and the methods of this invention are appropriate for isolation of DNA from samples that contain DNA, and in particular, from samples that contain cells such as bacteria cells, etc. The apparatus and the methods of the invention are especially suited for the separation of plasmid DNA of the molecular mass on the order of $10^6$ daltons from cells of *Escherichia coli* and for the separation of DNA of higher molecular weight, with molecular mass on the order of $10^8$ daltons. The apparatus and the methods of this invention can be used with cells other than those of *E. coli*; for example, they can be used with eukaryotic cells.

For the apparatus described above, the kind of adsorbent that is used to fill the column or columns, the kinds of reagents for sample treatment (for example, washing liquid and eluent), and the like are different depending upon the proposed use of the apparatus, and can be chosen so as to be appropriate for the intended use. As the packing (i.e., adsorbent) for column 1, there are, for example, ion-exchange gels, gels for reversed-phase systems, and gels for normal-phase systems. As ion-exchange gels there are DEAE-SEPHAROSE, QAE-Sepharose, CM-Sepharose, SP-SEPHAROSE, and the like. As gels for reversed-phase systems, there are, for example, $C_{18}$-silica gel, phenyl-silica gel, and so on. As gels for normal-phase systems, there is silica gel, etc. As other adsorbents that can be used, there are, for example, hydroxyapatite, starch, cellulose, and activated carbon. For example, when only double-stranded DNA (dsDNA) is to be selectively adsorbed from a sample that includes DNA, hydroxyapatite is suitable for use.

The pore size of the filters should be 5–100 μm, and is preferably within the limits of 20–70 μm. The pore size of 40 μm or less is particularly appropriate. If the pore size is less than 5 μm, the resistance of the filter becomes large, and this will not allow sufficient permeation of the sample into the adsorbent layer. If the pore size is more than 100 μm, the sample and the pretreatment media will not be retained in the reservoir, but will soon flow through the adsorbent layer, so that pretreatment (to be referred later) of the sample in the reservoir will not be carried out.

As pretreatment reagents that can be used in the pretreatment of samples (including the lysis of bacterial cells, the denaturation of protein, a step or steps of extraction, and the like), there are, for example, solutions containing detergent, salts, lytic enzymes, alkali, chelating agents, chaotropic agents, urea, and so on. Chelating agents or lytic enzymes can be used, for example, in methods by which DNA is to be isolated from cells, to weaken the cell walls in the step of cell lysis. As chelating agents, there are ethylenediaminetetraacetic acid (EDTA), 8-hydroxyquinoline, etc. As lytic enzymes, there are lysozyme, proteinase K, and so on. Detergents are used to lyse cell walls that have been weakened by the lytic enzymes or the chelating agents. As detergents, there are sodium dodecylbenzene sulfonate (SDS), TRITON X-100, NONIDET, and N-lauroylsarcosine. For example, SDS can be used at a concentration within the limits of 0.1–2%; the limits of 0.5–1% are preferable. Urea is generally used at the concentration of 2–8M. The concentration of 8M urea corresponds roughly to the concentration of urea at saturation. When the sample to be treated contains *E. coli*, the preferable composition of the pretreatment media is 0.2M NaOH, 1% SDS, 50 mM Tris.HCl (pH 8.0), 10 mM EDTA, and 1 mg/ml lysozyme. When the sample contains eukaryotic cells, the preferable composition of the pretreatment reagents is 1M NaCl, 1% SDS, 50 mM Tris.HCl (pH 8.0), 10 mM EDTA, and 1 mg/ml proteinase K.

As the eluent used in the elution step, a solvent that interacts strongly with at least one of the components (that are anion and cation) of the adsorbent, and preferably with both of the components, can be used. For example, when hydroxyapatite (the main ingredient of which is calcium phosphate) is used as a adsorbent for the isolation and purification of DNA, a solvent that interacts strongly with at least one and preferably both of the phosphate component and the calcium components of said calcium phosphate can be used, and in particular, a solution of salt that forms another salt substantially insoluble in water is appropriate. For such a salt, a salt with a small dissociation coefficient that has high affinity for nucleic acids such as DNA is preferred. Also, salts can be selected that are soluble in water and alcohols and that cannot be precipitated by ethanol. For example, when hydroxyapatite is used as the adsorbent, carbonic acid and organic acids such as formic acid, acetic acid, propionic acid, etc., are preferred as the anionic component. As the cationic component, ammonia; alkyl amines such as diethylamine, triethylamine, etc.; alkanol amines such as ethanolamine, propanolamine, etc.; and aromatic amines such as pyridine, aniline, etc. are suitable. As a solvent containing salts with these kinds of components, triethylamine-carbonate buffer is particularly suitable. Triethylamine-carbonate buffer is volatile, so with its use, it is possible to obtain DNA at a high degree of purification by the evaporation of the solvent in the eluate that contains the DNA or by the freeze-drying of the eluate.

The concentration of the eluent depends on the kind of the eluent that is used. For example, when triethylamine-carbonate buffer is used, the concentration should be 10 mM or more, and for preference 50 mM–2M; the most preferable limits are 100 mM–1M. With such a low concentration of 50 mM or less, it is possible to elute DNA from the hydroxyapatite.

In the washing liquid for use in the washing of the adsorbent, ordinarily, chelating agents, chaotropic agents, etc. are included. As these chelating agents and chaotropic agents, any of the reagents used in the pretreatment media can be employed.

With the use of the apparatus of this invention, biological samples can be treated in, for example, the following procedure, with reference to FIG. 1. First, sample from vessel 20 and pretreatment reagent from vessel 21 are supplied in this order to the reservoir 11 of column 1 by means of the supply means 3. In this reservoir 11, pretreatment of the sample is done. For samples that require no pretreatment, and for samples that have already been treated, the supply of the pretreatment reagent and the step of pretreatment are unnecessary. It is also acceptable if the sample and the pretreatment reagent are supplied directly to the reservoir 11 with the stopper 16 being removed. When pretreatment is carried out in the reservoir 11, it is effective to move the column by the column agitator 6 to accelerate the pretreatment that is carried out in reservoir 11. Next, a valve (not shown in the figure) provided in stopper 16 is opened, so that column 1 becomes an open system and so that the pretreated sample in reservoir 11 will permeate the adsorbent layer 1. Alternatively, valve 33 is turned so that air is made to flow to the reservoir by the pump 32 via a tube 31 that is open to the outside of this system, resulting in the permeation of the pretreated sample in the reservoir 11 to the adsorbent layer 10. Furthermore, an appropriate reagent is provided to the reservoir 11 from vessel 22 by means of the supply means 3, so that the pretreated sample in reservoir 11 is supplied to the adsorbent layer 10. Here, the substance in the sample that is to be measured or isolated adsorbs to said adsorbent layer 10. Next, washing reagent from vessel 23 is, if necessary, supplied to column 1 by means of the supply means 3, and washing takes place; then, the valve 33 is turned, and eluent is supplied from vessel 24 to column 1. In this way, the desired component that has adsorbed to the adsorbent layer 10 is eluted. The eluate is guided into a suitable apparatus for measurement and assayed; or the desired component is obtained by the pooling of certain eluate fractions. After elution, when the column is to be regenerated and reused, the valve 33 is turned again and regenerating reagent is supplied from vessel 25 to column 1. When the apparatus is equipped with plural columns, a large number of sample can be treated at the same time. Also, if a fraction collector is attached to column 1, it becomes possible for treatment to be continuous.

For example, by the method described above, when DNA is to be isolated from bacteria, a suspension that contains bacteria is used as a sample; and as the pretreatment reagent, a solution containing lytic enzymes such as lysozyme proteinase K, etc.; chelating agents such as EDTA, etc.; detergents such as SDS, etc.; and the like can be used. By the supply of this kind of pretreating reagents, the bacterial cells in the reservoir 11 of column 1 are lysed. That is, the cell walls of the bacteria are weakened by the lytic enzyme and the chelating agent and lysed by the detergent. The solution of lysed bacteria that is obtained is supplied to the adsorbent layer so that it comes into contact with the adsorbent. Hydroxyapatite or the like is suitable for use for the adsorbent, and for example, when a reagent of 0.15–0.25M phosphate buffer is used as solvent, the double stranded DNA (dsDNA) in the solution of lysed bacteria is selectively adsorbed. The RNA, proteins, carbohydrates, etc., that are also in the solution of lysed bacteria are eluted from column 1 without being adsorbed. The adsorbent layer with the DNA as adsorbate is supplied with washing reagent from vessel 23 so as to remove contaminants such as RNA, proteins, carbohydrates, etc., that are remaining in the adsorbent. Next, the adsorbent layer 10 is supplied with and brought into contact with eluent from vessel 24. For example, when hydroxyapatite carrying DNA as adsorbate is brought into contact with triethylamine-carbonate buffer, the carbonate binds to the calcium component of the hydroxyapatite, resulting in calcium carbonate, which is substantially insoluble in water. Also, the triethylamine binds to the phosphate component of the hydroxyapatite, resulting in a salt. Thus, the DNA is released from the hydroxyapatite. For example, when a column of hydroxyapatite is eluted with 2 bed volumes of triethylamine-carbonate buffer, almost all the adsorbed DNA can be recovered. The eluate collected in this way is generally treated by the ethanol precipitation method, resulting in purified DNA. Because the triethylamine carbonate in the solution is dissolved in ethanol, it does not precipitate with the DNA, and therefore does not lower the purity of the DNA obtained. Instead of by the ethanol precipitation method, the triethylamine carbonate can be removed (i.e., the removal of the salt can be achieved) by evaporation of the solvent under reduced pressure or by freeze-drying, by which means DNA of high purity is obtained.

The methods of this invention for the treatment of sample can be used not only for the isolation and purification of DNA as described above, but also for the dissolving and extraction of proteins.

EXAMPLE 1

Purification of Synthetic DNA Oligomers

By the solid-phase method, DNA oligomer with 15 nucleotides was synthesized. Of the protective groups for this DNA oligomer, the protective groups for the base portion and the phosphate portion were removed by the usual methods, and only the hydroxyl group at the 5'-terminus was left to be protected by dimethoxytrityl group. All of the procedures above were carried out by an automated DNA synthesizer. However, during the process of synthesis, DNA oligomers that had no protective group at the 5'-terminus (referred hereinafter as 5'-OH-DNA) were formed. These DNA oligomers were removed as impurities as described below.

The apparatus shown in FIG. 3 was used. There were 10 columns 1, and the fraction collector receptacle 71 had 10 collecting vessels 70. For the columns 1, columns with the internal diameter of 1 cm, filled with about 5 ml of $C_{18}$-silica gel and equilibrated with 50 mM triethylamine-acetate buffer (pH 8.0) were used. 0.5 ml of a solution of the DNA oligomers synthesized as described above was put into each of the reservoirs 11 of these columns 1. The solution of DNA oligomers mentioned above permeated into the adsorbent layer 10 from the reservoir 11 by its own weight and was adsorbed onto the adsorbent in the adsorbent layer 10. To these columns 1 with DNA oligomers as adsorbate, a column stopper 16 was attached, and then a supply means 3 and vessels 2 were connected. The vessel 20 was supplied with 50 mM triethylamine-acetate buffer (pH 8.0), vessel 21 with 15% acetonitrile-50 mM triethylamine-acetate buffer (pH 8.0), and vessel 22 with 35% acetonitrile-50 mM triethylamine-acetate buffer (pH 8.0).

Step 1 (Washing): Valve 33 was operated by control means 4 so as to supply 5 ml of 50 mM triethylamine-acetate buffer (pH 8.0) to the columns 1. This buffer was supplied from vessel 20 by means of pump 32, passing through tubes 31 and 30. This buffer washed the adsorbent layer 10 in the columns 1.

Step 2 (Washing): Next, control means 4 switched valve 33 to vessel 21. From this vessel 21, in the same way, columns 1 were supplied with 10 ml of 15% acetonitrile-50 mM triethylamine-acetate buffer (pH 8.0), which washed the adsorbent layer 10 of column 1. This washing procedure eluted the 5'-OH-DNA that were impurities and that had adsorbed to the adsorbent in the adsorbent layer 10.

Step 3 (Elution): Next, control means 4 operated to switch valve 33 to vessel 22. From this vessel 22, in the same way, column 1 was supplied with 5 ml of 35% acetonitrile-50 mM triethylamine-acetate buffer (pH 8.0). This eluted the 5'-dimethoxytritylated oligo-DNA (referred hereinafter to as 5'-DMTr-DNA) that had adsorbed to the adsorbent in adsorbent layer 10.

The results of elution of the 5'-DMTr-DNA were monitored by the absorbance of ultraviolet light at 260 nm on a UV spectrophotometer. The results of these purification steps in terms of the elution results are shown in FIG. 4.

Figure 4:
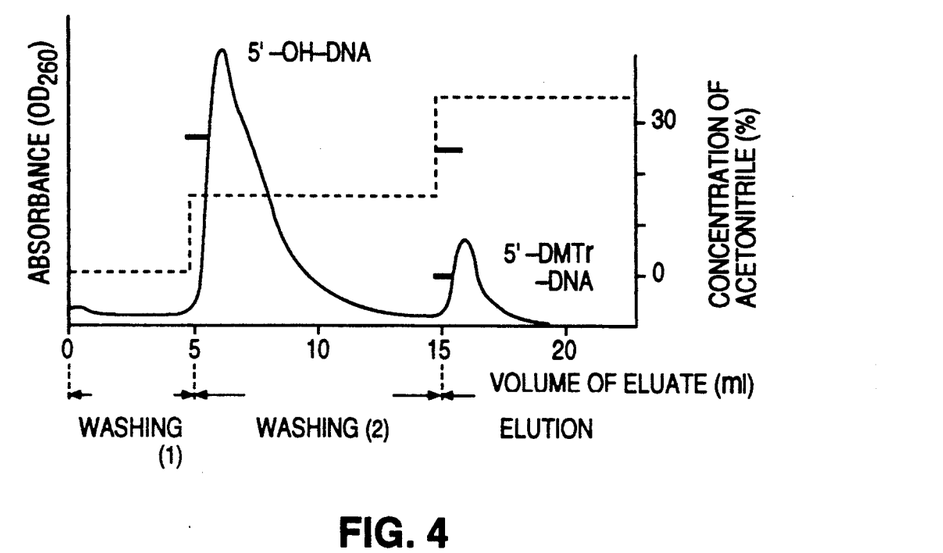
FIG. 4 is a graph that shows the relationship of the volume of eluate from the column and the absorbance of ultraviolet light at 260 nm in Example 1.

As can be seen from FIG. 4, Step 2 of washing elutes the 5'-OH-DNA, and the elution step elutes the 5'-DMTr-DNA.

By the procedure described above, 10 samples were supplied to 10 columns and were treated at the same time. The results obtained showed that all of the samples gave almost the same elution results, which shows that this apparatus for the treatment of samples was effective for use in the purification of DNA oligomers.

EXAMPLE 2

Purification of Mouse Monoclonal Antibody

Column 1, with an inner diameter of 8 mm, was packed with 1 ml of AFFI-GEL Protein A (Bio-Rad Laboratories; affinity gel fixed with Protein A and equilibrated with 10 mM sodium phosphate in 0.15M NaCl buffer (pH 8.2)), resulting in an adsorbent layer 10. To column 1 packed in this way with adsorbent, a column stopper 16 was attached, and then a supply means 3 and vessels 2 were connected, so as to construct the apparatus shown in FIG. 1. Vessel 20 was supplied with mouse serum diluted twofold, vessel 21 with 10 mM sodium phosphate-0.15M NaCl buffer (pH 8.2), vessel 22 with a 0.1M glycine.HCl buffer (pH 3.0), and vessel 23 with 10 mM sodium phosphate-0.15M NaCl buffer (pH 8.2).

Step 1 (Washing): Control means 4 operated the valve 33, switching said valve so as to supply column 1 with 1 ml of the mouse serum. This mouse serum was supplied from vessel 20 through tubes 31 and 30 by means of pump 32. This mouse serum permeated into the adsorbent layer 10 from the reservoir 11, and adsorbed to the adsorbent. Next, the control means 4 switched valve 33 to vessel 21. From this vessel 21, in the same way, column 1 was supplied with 20 ml of 10 mM sodium phosphate-0.15M NaCl buffer (pH 8.2), and this washed the adsorbent layer 10 to which the mouse serum had adsorbed.

Step 2 (Elution): Next, the control means 4 switched the value 33 to vessel 22. From this vessel 22, in the same way, column 1 was supplied with 10 ml of the 0.1M glycine.HCl buffer (pH 3.0), which eluted the monoclonal antibody in the mouse serum that had adsorbed to the adsorbent in the adsorbent layer 10.

Step 3 (Washing): After the elution step, in order to regenerate column 1, 20 ml of 10 mM sodium phosphate-0.15M NaCl buffer (pH 8.2) was supplied from vessel 23. The column 1 was regenerated by being washed with the buffer.

In these steps of the procedure, the operation of the valve, the adjustment of flow from the pump, the movements of the fraction collector, and the like, were all controlled by a microcomputer (which is the control means 4). The elution of the monoclonal antibody in the mouse serum was monitored by the absorbance of ultraviolet light at 280 nm on a UV spectrophotometer. The results of the elution pattern by these steps are shown in FIG. 5.

Figure 5:
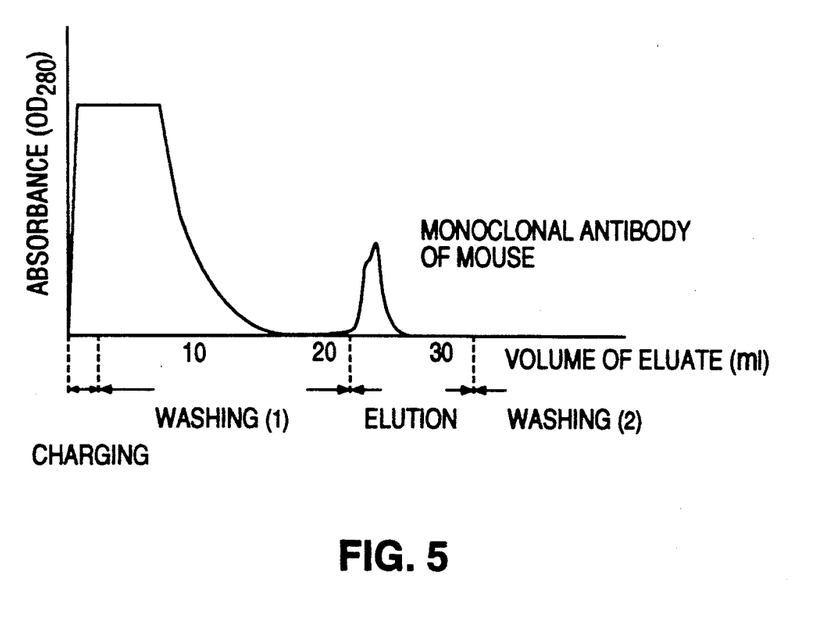
FIG. 5 is a graph that shows the relationship of the volume of eluate from the column and the absorbance of ultraviolet light at 280 nm in Example 2.

It can be seen from FIG. 5 that by this procedure, monoclonal antibody in the mouse serum were eluted with high purity.

EXAMPLE 3

Purification of Serum Albumin

Column 1, with an inner diameter of 15 mm and a length of 50 mm, was packed with 5 ml of ion-exchange resin (QAE-SEPHADEX A50; Pharmacia) resulting in an adsorbent layer 10. Then 1 ml of bovine serum was put into the reservoir 11 of column 1 as the sample. This bovine serum permeated into the adsorbent layer 10 from the reservoir by its own weight, and was adsorbed to the adsorbent. To the column 1 that contained bovine serum adsorbed in this way, a column stopper 16 was attached, and then a supply means 3 and vessels 2 were connected, so as to construct the apparatus shown in FIG. 1. Vessels 20, 21, 22, and 23 were supplied with Tris.HCl buffer at the concentrations of 0.1, 0.2, 0.3, and 0.4M, respectively. Then, control means 4 operated valve 33, and supplied 10 ml of 0.1M Tris.HCl buffer to column 1. Said buffer was supplied by pump 32 from vessel 20 through tubes 31 and 30. In the same way, 10 ml of the Tris.HCl buffer at the concentrations of 0.2, 0.3, and 0.4M was supplied in this order from vessels 21, 22, and 23, respectively, to column 1. The supply of the Tris.HCl buffer at the concentrations of 0.1, 0.2, 0.3, and 0.4M to the column brought about elution steps 1, 2, 3, and 4, respectively. In elution step 1, immunoglobulin G (IgG) was eluted, and in the other elution steps, serum albumin was eluted. Also, for each concentration of Tris.HCl buffer, a different amount of serum albumin was eluted. The elution of the serum albumin in bovine serum was monitored by the absorbance of ultraviolet light at 280 nm measured by a UV spectrometer. This purification gave the elution pattern shown in FIG. 6.

Figure 6:
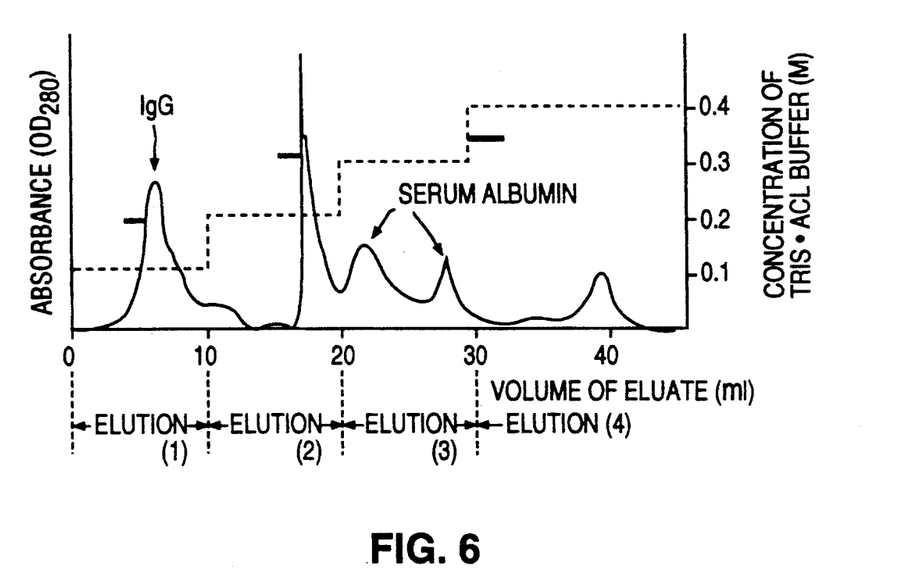
FIG. 6 is a graph that shows the relationship of the volume of eluate from the column and the absorbance of ultraviolet light at 280 nm in Example 3.

It can be seen from FIG. 6 that the amount of serum albumin eluted by each concentration of Tris.HCl buffer was different. In elution step 1, no serum albumin was eluted, but IgG was.

EXAMPLE 4

Purification of DNA Radiolabelled by the Nick Translation Method

Column 1, with an inner diameter of 5 mm was packed with about 5 ml of $C_{18}$-silica gel that was equilibrated with 50 mM Tris.HCl buffer (pH 7.5), resulting in an adsorbent layer 10. One hundred nanograms of DNA was labelled with [$^{32}$P]dCTP by the usual method (i.e., the nick translation method), and the reaction mixture (100 μl) was charged into the reservoir 11 of this column 1. This reaction mixture containing radiolabelled DNA permeated into the adsorbent layer 10 from the reservoir 11 by its own weight, where it adsorbed to the adsorbent. To column 1, which contained radiolabelled DNA adsorbed in this way, a column stopper 16 was attached, and then supply means 3 and vessels 2 were connected, to construct the apparatus shown in FIG. 1. Vessel 20 was supplied with 10 mM Tris.HCl buffer (pH 7.5) containing 1 mM EDTA, and vessel 21 was supplied with 50% methanol.

Step 1 (Washing): Valve 33 was operated by the use of control means 4, so that 5 ml of the 10 mM Tris.HCl buffer (pH 7.5) containing 1 mM EDTA was supplied to column 1. Said buffer was supplied by pump 32 through tubes 31 and 30. This buffer washed the adsorbent layer 10 of column 1. This washing step washed away the salts and $^{32}$P-dCTP that had not been adsorbed. The radiolabelled DNA and proteins such as enzymes, adsorbed strongly to the adsorbent and were not washed away. Next, by the use of control means 4, valve 33 was switched to vessel 21.

Step 2 (Elution): From this vessel 21, in the same way, 1 ml of 50% methanol was supplied to column 1, which eluted the radiolabelled DNA that had been adsorbed onto the adsorbent layer 10 of the column 1. With this buffer, only the radiolabelled DNA was eluted, and the impurities mixed with the DNA, such as proteins, including enzymes, etc., were not eluted. The reason is that these proteins had been adsorbed strongly to the adsorbent.

Figure 7:
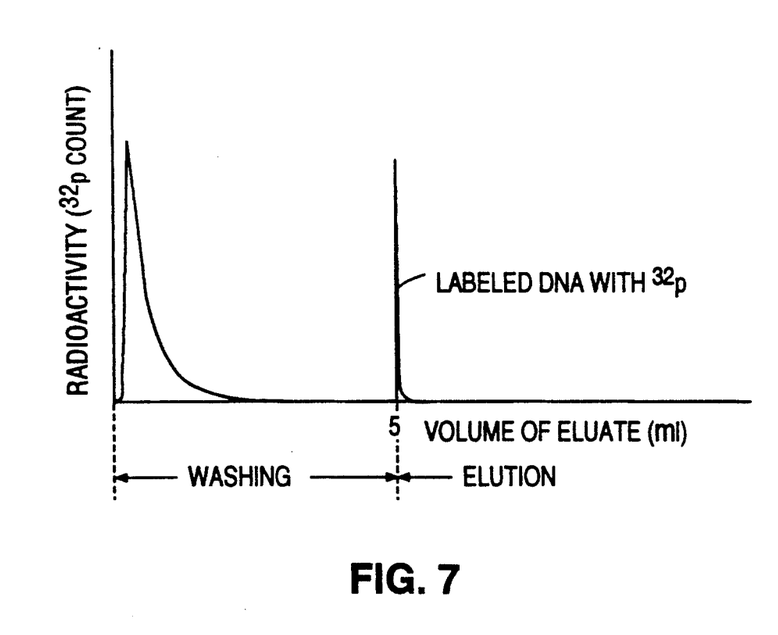
FIG. 7 is a graph that shows the relationship of the volume of eluate from the column and the radioactivity (measured as the $^{32}P$ count) in Example 4.

The elution of the radiolabelled DNA was monitored by the radioactivity (measured as the $^{32}$P count). This elution pattern is shown in FIG. 7. It can be seen from FIG. 7 that in the elution step, the $^{32}$P count increased greatly. The $^{32}$P count also increased at the beginning of the washing step, which reflects the radioactivity of the radiolabelled substances of low molecular weight such as $^{32}$P-dCTP and the decomposition product thereof. These substances were not adsorbed to the adsorbent.

EXAMPLE 5

Isolation of Plasmid DNA from a Lysate of *E. coli* Cells (A) Culture of *E. coli*

*E. coli* HB 101 cells that contained plasmid pBR322 were cultured overnight on 5 ml of LB medium. A portion (1.5 ml) of this culture broth was centrifuged for 5 minutes at 5000 rpm, and a precipitate of cells was obtained.

(B) Preparation of lysate

The cells obtained in section A above were suspended in 250 μl of 2×TE [20 mM Tris.HCl-10 mM EDTA (pH 8.0)]. This suspension was put into the reservoir 11 of column 1 shown in FIG. 2A, in which the valve 19 was closed. A column stopper 16 was attached to the column 1, and then tubes 17 and 30 and valve 18 were connected also. Tube 30 was attached to supply means 3 and vessels 2, to construct the apparatus shown in FIG. 1, except that the column 1 was of another type which was mentioned above, that a fraction collector was provided, and that another tube 31 that was open to the outside of this system was provided. In the apparatus, the control means 4 controlled the functions of pump 32, valve 33, valves 18 and 19 (not shown in FIG. 1), agitator 6, and fraction collector (not shown in FIG. 1). First, the valve 18 of column 1 was opened, making the column an open system, and then 50 μl of 50 mM Tris.HCl buffer containing lysozyme in the concentration of 1 mg/ml was added to the reservoir 11 of said column 1 via the tube 30 from vessel 20. Valve 18 was closed, making column 1 a closed system, and the cells were agitated for 10 minutes at room temperature to give a lysate.

Next, valve 18 was opened, making it an open system, and 20 μl of 0.5M EDTA was supplied to the reservoir 11 of column 1 via tube 30. Valve 18 was closed, making the column 1 a closed system, then the column 1 was gently agitated for 10 minutes at room temperature. In the following steps, when a reagent was supplied to the reservoir 11, valve 19 was closed and valve 18 was opened so as to make the column 1 an open system, and when any treatment of the sample (e.g., lysis) was carried out in the reservoir 11, valve 18 and 19 were closed so as to make column 1 a closed system. After the agitation, 10 μl of 2% Triton X100 was added through tube 30, and the mixture was left at room temperature for 45 minutes. During this time, the column was continuously agitated gently. Column stopper 16 was removed and about 1 μCi of plasmid DNA (pBR322) labelled with $^3$H in vitro was added to the reservoir of column 1 for the purpose of calculation of the yield. Then, the column stopper 16 was attached to column 1 again.

(C) Purification of DNA (C-1) Column step (adsorption)

To the solution containing lysed bacterial cells (i.e., the lysate) in the reservoir 11, which solution was obtained in section B above, 8 volumes of 9M urea-0.27M phosphate buffer (pH 7.0) containing 1% SDS was added. This buffer was supplied from vessel 22 via tube 30. Then, valve 19 was opened and valve 18 was closed, making reservoir 11 a closed system, and this mixture was pushed into the adsorbent layer at the rate of 5 ml/hour by compressed air provided from outside by pump 32 via tubes 31 and 30. At the time when all of the lysate solution in the reservoir 11 had just been pushed into the adsorbent layer 10, control means 4 controlled valve 18, to open, and valve 19, to close, so that air was not pushed into the adsorbent layer 10. Bacterial components in the lysate were adsorbed to the adsorbent (which was 0.5 ml of hydroxyapatite).

(C-2) Column step (Step 1 of washing)

The column described above was washed with about 20 ml of 8M urea-0.24M phosphate buffer (pH 7.0) supplied at the rate of 20 ml/hour for about one hour through tube 30 from vessel 23, and thus washing was done. The buffer was continued to be supplied until the optical density at 260 nm ($OD_{260}$) was almost 0. During the process, impurities such as RNA, proteins, carbohydrates, etc. were removed.

(C-3) Column step (Step 2 of washing)

Next, about 10 ml of TE [10 mM Tris.HCl-1 mM EDTA buffer (pH 7.5)] was supplied from vessel 24 via tube 30 at the rate of 20 ml/hour for 30 minutes, and the urea-phosphate buffer used in section C-2 above for washing was washed away.

(C-4) Column step (Elution)

Figure 8:
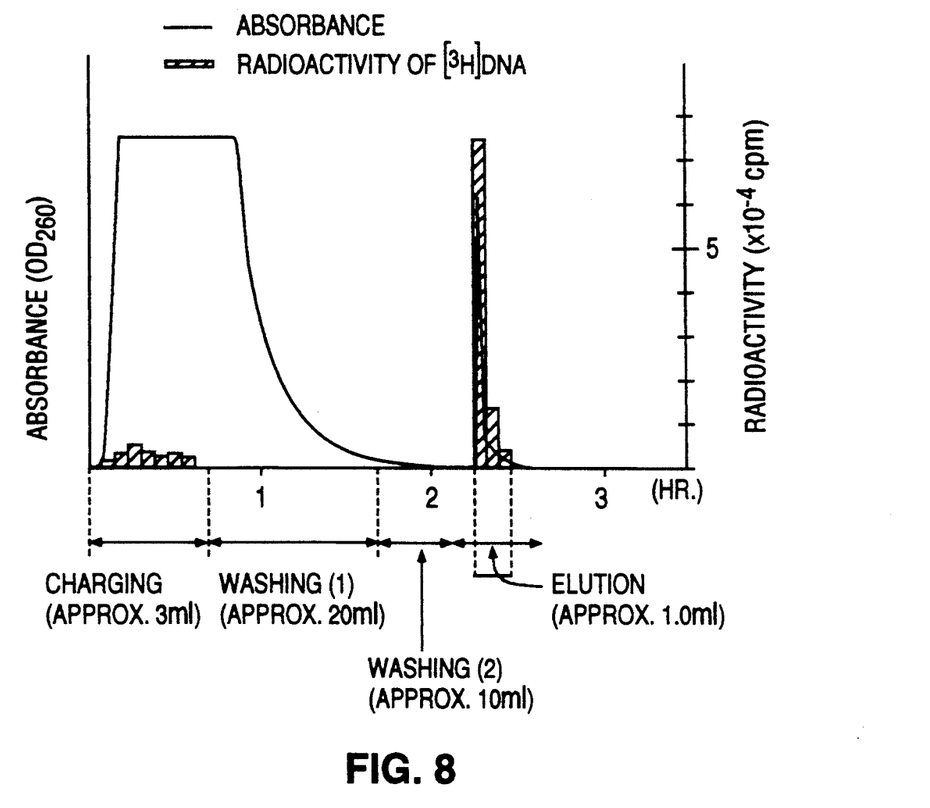
FIG. 8 is a graph that shows the relationship of the volume of eluate from the column and the absorbance of ultraviolet light at 260 nm in Example 5.

Next, from vessel 25, 0.1M triethylamine.carbonate buffer (pH 8.0) was sent through column 1 via tube 30 at the flow rate of 5 ml/hour. An ultraviolet (UV) monitor was connected at the outlet of column 1 and the absorbance at the wavelength of 260 nm was monitored, with the results plotted as a curve in FIG. 8. FIG. 8 shows that most of the plasmid DNA was eluted in the eluate at the beginning of elution with the fractions from 0.2 to 1.2 ml. The radioactivity of each fraction collected was measured, and the recovery of $^3$H-labeled plasmid contained in each fraction was calculated. These results are shown as a histogram in FIG. 8. FIG. 8 shows that more than 95% of the plasmid pBR322 DNA was recovered.

(C-5) Isolation of DNA and evaluation of its purity

Figure 9:
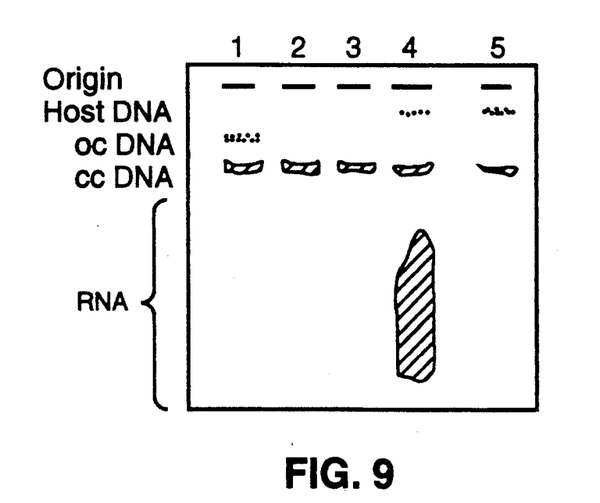
FIG. 9 is the electrophoretic patterns of purified DNA obtained in Examples 5 and 6 and in the comparative example.

To about 1 ml of the eluate obtained, 0.1 ml of 3M sodium acetate was added, and then 2 ml of ethanol was added to precipitate the plasmid DNA (pBR322). The amount of the DNA was 4 μg. About one-fifth of this plasmid DNA was studied by agarose gel electrophoresis. The results of electrophoresis are shown in FIG. 9, lane 2 (lane 1 in FIG. 9 shows marker plasmid DNA (pBR322)). RNA was not detected, and a trace amount of host DNA was found. The amount of host DNA was less than the amount of the purified DNA (the amount of host DNA of which was 5% or less) obtained by a conventional method with the use of ribonuclease. For comparison, an electrophoretic pattern of purified DNA obtained by the conventional method (in the comparative Example) is shown in FIG. 9, lane 5. In FIG. 9, open circular DNA (ocDNA) refers to nicked pBR322, and closed circular DNA (ccDNA) refers to pBR322 that is not nicked.

Next, the eluate collected was assayed for protein. The amount of protein in the eluate was below the lower limit of detection, 20 ng/ml. Thus, the DNA obtained was substantially pure. This DNA was completely digested by the restriction enzyme HinfI, so its purity was satisfactory.

EXAMPLE 6

The same procedures were carried out as in Example 5 with the apparatus mentioned in Example 5, except that the alkali method was used to lyse the *E. coli* cells.

(A) Culture and lysis of *E. coli*

Cells of *E. coli* were collected from a 1.5-ml portion of the culture broth by the same procedures as in Example 5A. To the cells, 100 μl of 2×TE [20 mM Tris.HCl-10 mM EDTA buffer (pH 8.0)] was added to make a suspension. This suspension was put into the reservoir 11 of column 1. A column stopper 16 was attached to column 1, and tubes 17 and 30 and valve 18 were connected, so as to construct the apparatus used in Example 5. Next, 200 μl of a solution of 50 mM Tris.HCl buffer with sodium hydroxide at the final concentration of 0.2M and SDS at the final concentration of 0.1% was added to this reservoir 11. Valve 18 was closed, making the column 1 a closed system, and column 1 was agitated for 10 minutes at room temperature to lyse the cells.

Next, the solution in reservoir 11 (which was a strong alkali) was neutralized with 150 μl of 3M potassium acetate (pH 5.0). To this solution, for the purpose of calculation of the recovery, about 0.1 μCi of pBR322 plasmid DNA that was radiolabelled with $^3$H in vitro was added.

(B) Isolation of DNA

Column 1 was washed and the eluents were supplied in the same way as in Example 5. Most of the plasmid DNA was collected in the first fractions from 0.2–1.2 ml after the start of elution. The yield of DNA was 95% or more judged from the radioactivity of the $^3$H-labeled plasmid DNA. These steps were controlled completely by a computer, and the procedure was finished in about 2 hours.

To about 1 ml of the eluate obtained, 3M sodium acetate was added, and then ethanol was added to precipitate DNA. Thus, 3 μg of plasmid DNA (pBR322) was obtained. This plasmid DNA was studied by agarose electrophoresis. The electrophoretic pattern obtained is shown in FIG. 9, lane 3. RNA was not detected, and the amount of host DNA was less than the amount of the purified DNA obtained by a conventional method. The host DNA was difficult to detect by ethidium bromide staining. For comparison, an electrophoretic pattern obtained in the comparative example, done by the conventional method, is shown in FIG. 9, lane 4.

Next, the solution obtained was assayed for protein. The amount of protein was below the detection limit of 20 ng/ml, which showed that the purity of the DNA was satisfactory. This DNA was completely digested by the restriction enzyme HinfI, and thus its purity was satisfactory.

EXAMPLE 7

By the method of H. Okayama, and P. Berg, (Mol. Cell. Biol., 2, 161(1982)), cDNA that corresponded to the mRNA for β-globin from the reticulocytes of rabbits was prepared, and a cDNA library was made by the insertion of the cDNA into the Okayama-Berg vector. This cDNA library was then introduced into competent cells of the strain *E. coli* HB101 that were pretreated with the calcium chloride, by which the *E. coli* cells were transformed. The *E. coli* obtained by this treatment were grown on LB agar reagent containing ampicillin, and colonies were formed. These colonies were transferred onto a filter, and with the use of an oligo-DNA probe that corresponded to the β-globin of rabbits, screening was carried out by the colony hybridization method. Ten positive colonies were obtained. These ten colonies of *E. coli* contained Okayama-Berg plasmids that incorporated inserts of the cDNA of rabbit β-globin.

The ten colonies were cultured, and the cells were then obtained by centrifugation of 1.5 ml of the culture broth. These cells were suspended in 100 μl of a 2×TE buffer [20 mM Tris.HCl-10 mM EDTA buffer (pH 8.0)]. The apparatus in FIG. 3, which was equipped with ten columns 1 shown in FIG. 2(A), was used, and the ten kinds of suspensions mentioned above were each put into the reservoir 11 of one of the columns 1. The plasmids were isolated from the *E. coli* cells and were purified in a method similar to that of Example 6. About 2–3 μg of each kind of plasmid was obtained. The DNA obtained had in it very little host DNA, as in Example 6, and the amounts of RNA and protein in it were below the detection limits, which showed that purity was satisfactory. This DNA was digested by the restriction enzymes PvuII and PstI, and its purity was satisfactory.

COMPARATIVE EXAMPLE

The above examples were all of the use of treatment methods for biological samples by an automated apparatus that makes use of a small column or columns, based on the principles of liquid chromatography. Next, an example of the purification of DNA by the alkali method (i.e., the conventional method) will be shown.

(A) Culture and lysis of *E. coli*

With the use of the same reagents as were used in Example 6A, the conventional manual procedure was employed to make a lysate, and to this, $^3$H-labeled pBR322 DNA was added. To this, an equal volume of a phenol-chloroform mixture (1:1) was added to extract and remove protein, and the supernatant was collected. To this, an equal volume of isopropanol was added so that a precipitate was formed. The precipitate was centrifuged for 10 minutes at 15000 rpm, and was washed with 70% ethanol. The washed precipitate was then dried under reduced pressure so that the DNA fraction was obtained. To this DAN fraction, 50 $\mu$l of TE buffer was added to dissolve the DNA. Next, to this solution, 2 $\mu$l of solution containing ribonuclease (1 mg/ml) was added, and the mixture was left at 37° C. for 1 hour to decompose the RNA. To this mixture, a 0.2-volume of an aqueous solution of 5M NaCl and a 0.33-volume of an aqueous solution 30% polyethylene glycol 6000 were added, and the mixture was chilled at $-10$° C. for 1 hour. The precipitate (which was plasmid DNA) that was formed was collected by centrifugation for 10 minutes at 15000 rpm. Because the decomposed RNA would not precipitate, it was readily removed. The DNA obtained was dissolved in 50 $\mu$l of TE buffer, and to this, 5 $\mu$l of 3M NaCl aqueous solution was added. To this mixture, 100 $\mu$l of 99% ethanol was added, and the whole was chilled at $-78$° C. for 10 minutes. The mixture was then centrifuged for 10 minutes. The mixture was then centrifuged for 10 minutes at 15000 rpm, and the DNA was collected. By this procedure, the polyethylene glycol was removed. The DNA obtained was washed with 70% ethanol again, and dried under reduced pressure. The yield of DNA was 3 $\mu$g. The electrophoretic patterns of the DNA purified with and without ribonuclease are shown in FIG. 9, lanes 4 and 5, respectively. When ribonuclease treatment was not done, a large amount of RNA contaminated the DNA. When ribonuclease treatment was done, RNA was not detected, but the treatment process required an additional 3 hours.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An automated method for a column separation and/or purification of predetermined components in biological samples by the use of an automated apparatus, said apparatus comprising:
   a) at least one column comprising an upper and a lower part, wherein an adsorbent layer is sandwiched between two porous filters in the bottom part of said column, said filters not allowing permeation of the samples into the adsorbent layer, but allowing permeation of the predetermined components in the samples, and wherein the top part of the column forms a reservoir;
   b) at least three vessels connected via supply means to said reservoir, said vessels, respectively, being disposed so as to contain (i) said samples, pretreatment liquid for lysing said samples, (ii) washing liquid for use in the washing of the adsorbent, and (iii) eluants to recover said predetermined components of said samples from said adsorbent, said reservoir being a space where said samples are lysed with said pretreatment liquid prior to adsorption of said components of said samples to said adsorbent layer;
   c) two valve means, a first valve means at the upper side of the reservoir for opening said column to atmospheric pressure and a second valve means at the outlet of said column for retaining contents of said column;
   d) a collecting means for the separated/purified predetermined components; and
   e) a means for automatically controlling said supply means and collecting means;
   said method comprising the steps of:
   i) supplying said samples from said corresponding vessel to said reservoir via said supply means or supplying said samples directly to said reservoir;
   ii) supplying said pretreatment liquid from said corresponding vessel to said reservoir via said supply means or supplying said pretreatment liquid directly to said reservoir, so that said samples are lysed with said pretreatment liquid within said reservoir prior to adsorption of said predetermined components of said sample to said adsorbent layer;
   iii) allowing said lysed samples to permeate the adsorbent layer of said column, which comprises the steps of opening said second valve at the outlet of said column, closing said first valve at the upper side of the reservoir and making air flow to the reservoir by said supply means, so that said column becomes an open system and the lysed samples in the reservoir permeate into the adsorbent layer, and which causes said adsorbent to adsorb components of said lysed samples to be separated and/or purified; and
   iv) supplying washing liquid to the adsorbent layer from the vessels via the supply means, so that said adsorbent layer is washed;
   v) supplying eluants to the adsorbent layer via the supply means to cause the predetermined components to be eluted from the adsorbent layer, said supply of the samples, the pretreatment liquid, the washing liquid and the eluants by the use of said supply means being controlled by said controlling means; and,
   vi) collecting the separated/purified predetermined components by the use of said collecting means being controlled by said controlling means.

2. The method according to claim 1, wherein said biological samples contain cells, and wherein said method further comprises lysing said cells in said reservoir, by the use of said pretreatment liquid.

3. The method according to claim 2, wherein said predetermined component of said biological samples is DNA, and said DNA is purified during said automated method.

4. The method according to claim 3, wherein said adsorbent is hydroxyapatite.

5. The method according to claim 4, wherein DNA is eluted by eluant that is a salt solution that reacts with said hydroxyapatite.

6. The method according to claim 5, wherein said salt solution contains ammonia and/or an amine selected from the group consisting of diethylamine, triethylamine, ethanolamine, propanolamine, pyridine and aniline as a cation constituent.

7. The method according to claim 5, wherein said salt solution contains carbonic acid and/or an organic acid selected from the group consisting of formic acid, acetic acid and propionic acid as an anion constituent.

8. The method according to claim 5, wherein said salt solution is triethylamine.carbonate buffer.

* * * * *